United States Patent [19]

Rainin

[11] 4,245,859
[45] Jan. 20, 1981

[54] TWEEZER DEVICE FOR MANIPULATION OF SOFT CONTACT LENSES

[76] Inventor: Edgar A. Rainin, 20 Shawn Ct., Danville, Calif. 94526

[21] Appl. No.: 78,310

[22] Filed: Sep. 24, 1979

[51] Int. Cl.³ .............................................. A61F 9/00
[52] U.S. Cl. ................................................ 294/1 CA
[58] Field of Search ............. 294/1 CA, 16, 33, 99 R; 51/216 LP, 217 L; 81/43; 128/303 R, 321; 206/5.1; 351/160

[56] References Cited

U.S. PATENT DOCUMENTS 3,265,068  8/1966  Holohan ................................. 294/16
4,126,345 11/1978  List ..................................... 294/1 CA Primary Examiner—James B. Marbert
Attorney, Agent, or Firm—Bielen and Peterson

[57] ABSTRACT

A tweezer device for manipulation of soft contact lenses employing a pair of legs connected to one another such that an end of each leg is generally in opposition to one another. Each leg includes a capped end portion having an end surface which spans a first and second tip where one of the tips extends further from the device than the other tip. Each cap also includes a cap covering both tips and is constructed of a soft material having an elastic memory.

4 Claims, 5 Drawing Figures

TWEEZER DEVICE FOR MANIPULATION OF SOFT CONTACT LENSES

BACKGROUND OF THE INVENTION

The present invention relates to a novel tweezer device for the manipulation of soft contact lenses.

Soft contact lenses are constructed of flexible and liquid permeable material such as 2-hydroxyethyl methacrylate. Soft contact lenses are more susceptible to contamination than hard contact lenses as a result of the high liquid absorbency. Insertion and removal of soft contact lenses must be performed in an aseptic manner for the prevention of eye infections. In this regard, reference is made to U.S. Pat. No. 4,079,976, issued to Rainin et al, which described a device which successfully permits the insertion and removal of soft contact lenses.

It has been found that an additional device is necessary for the placement of the soft contact lens on the insertion device, such as the Rainin et al device. It has also been found that the removal of soft contact lenses is more easily accomplished with the human hands. Unfortunately, human hands often contaminate soft contact lenses.

A device for the removal and manipulation of soft contact lenses aseptically is necessary.

SUMMARY OF THE INVENTION

In accordance with the present invention a novel and useful device for the manipulation, and especially the removal of, soft contact lenses is provided.

The device of the present invention utilizes a pair of relatively rigid legs connected at each legs end portion to form a tweezer-like device. Each leg has a free end portion which includes an end surface. The device may also include means for resisting any force which tends to bring the free ends of the legs together. Such means may take the form of a spring or merely forming the connected legs from resilient material. Each of the pair of legs may also include a gripping or roughened portion spaced from the free end to permit the user to grip the device with the minimization of slippage.

Each end surface of each leg is covered by a cap constructed of soft material having an elastic memory. Each cap includes a first tip, a second tip, and an end surface therebetween. The tip of each leg extends further from the point of interconnection of both legs than the second tip. The cap and surface spans the first and second tips and may be flat or curved to conform to the surface of the soft contact lens which is in place on an eye.

In addition, the tweezer device may be constructed such that the end portion of each of the legs includes a shoulder which bears on a portion of the cap. Also, the end surface of each leg may roughly parallel an inner-surface of the cap, which in turn could parallel the outer-surface of the cap. In this manner, the cap would be fully supported by the end portion of the leg.

It may be seen that a novel and useful tweezer device for the removal of contact lenses has been described.

It is therefore an object of the present invention to provide a tweezer device for manipulation of soft contact lenses which may be employed for the removal of a soft contact lens in place on an eye for use with a mirror which affords a full view of the removal process.

It is another object of the present invention to provide a tweezer device for the manipulation of soft contact lenses which may be employed in an aseptic system for the insertion, cleaning, and removal of soft contact lenses.

It is yet another object of the present invention to provide a tweezer device for the manipulation of soft contact lenses which includes a soft portion intended for touching the soft contact lens without inflicting any damage thereto.

It is another object of the present invention to provide a tweezer device for manipulation of soft contact lenses which combines a rigid portion with a flexible portion thereof for ease of handling.

It is yet another object of the present invention to provide a tweezer device for manipulation of soft contact lenses which is sized to prevent the interference of finger nails during insertion, removal and cleaning of soft contact lenses.

The invention possesses other objects and advantages especially as concerns particular characteristics and features thereof, which will become apparent as the specification continues.

For a better understanding of the invention, reference is made to the following detailed description.

DESCRIPTION OF THE PREFERRED EMBODIMENTS

Various aspects of the present invention will evolve from the following detailed description of the preferred embodiments thereof, which should be taken in conjunction with the heretofore described drawings.

Figure 1:
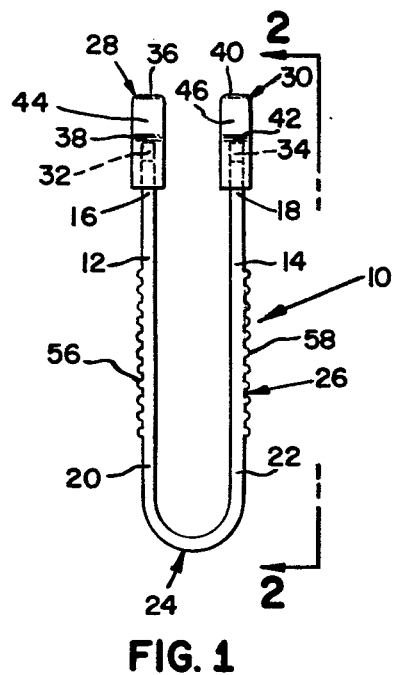
FIG. 1 is a front elevational view of the device.
Figure 2:
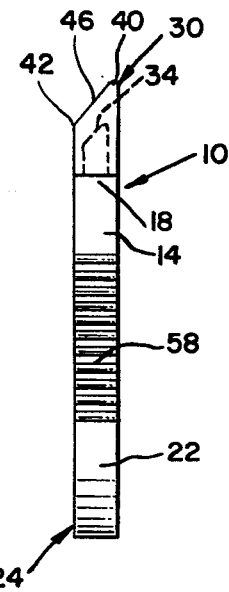
FIG. 2 is a view taken along line 2—2 of FIG. 1.
Figure 3:
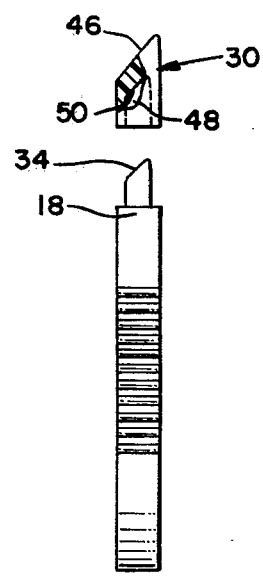
FIG. 3 is an exploded side view of the device showing a cut away portion of the cap.

With reference to the drawings, the invention as a whole is depicted by reference character 10 and includes as one of its elements a pair of relatively rigid legs 12 and 14. Legs 12 and 14 include first end portions 16 and 18 and second end portions 20 and 22 respectively, FIG. 1. Means 24 connects second end portions 20 and 22 of legs 12 and 14 together to form, in the embodiment shown in the drawings, a roughly horseshoe-shaped unit. Legs 12 and 14 and means 24 may be molded continuously, as shown, and exhibit resiliency such that device 10 includes means 26 for resisting force tending to bring legs 12 and 14 together, especially at end portions 16 and 18. Legs 12 and 14 may be constructed of wood, metal, plastic, and the like and is preferably constructed of material which is capable of being sterilized in autoclave or by chemical methods. Each leg 12 and 14 includes a cap 28 and 30 which fits snugly on the end portions 16 and 18 thereof. As may be seen from FIG. 1, end portions 16 and 18 of legs 12 and 14 include end surfaces 32 and 34. Each cap 28 and 30 includes a pair of tips 36 and 38, and 40 and 42 respectively, FIGS. 1 and 2. It should be noted that any of the tips 36, 38, 40, or 42 may be slightly rounded but generally depict a change in orientation or curvature of caps 28 and 30. Each cap also includes an end surface 44 and 46 which generally spans the distance between tips 36, 38, 40, and 42. With reference to FIG. 2, it may be seen that tip 40 extends further from first end portion 18 of leg 14 than tip 42. The same relationship applies to first leg 12. Cap 30 of end surface 46 obtains support from end surface 34 of end portion 18 of leg 14. Again, the same relationship applies to leg 12. Caps 28 and 30 are constructed of soft material having an elastomeric memory such as silicon, rubber, and like materials, and include a hollow portion 48, FIG. 3 (one not shown with reference to cap 28). Inner surface 50 may substantially parallel end surface 34 of end portion 18 of leg 14 such that the cap portion between inner surface 50 and end surface 46 receives solid support. Each cap 28 and 30 includes an inner edge 52 and 54, whose function will be explained hereinafter. Each leg 12 and 14 also has a roughened portion 56 and 58 which permits the sure gripping of tweezer device 10 while in use.

Figure 4:
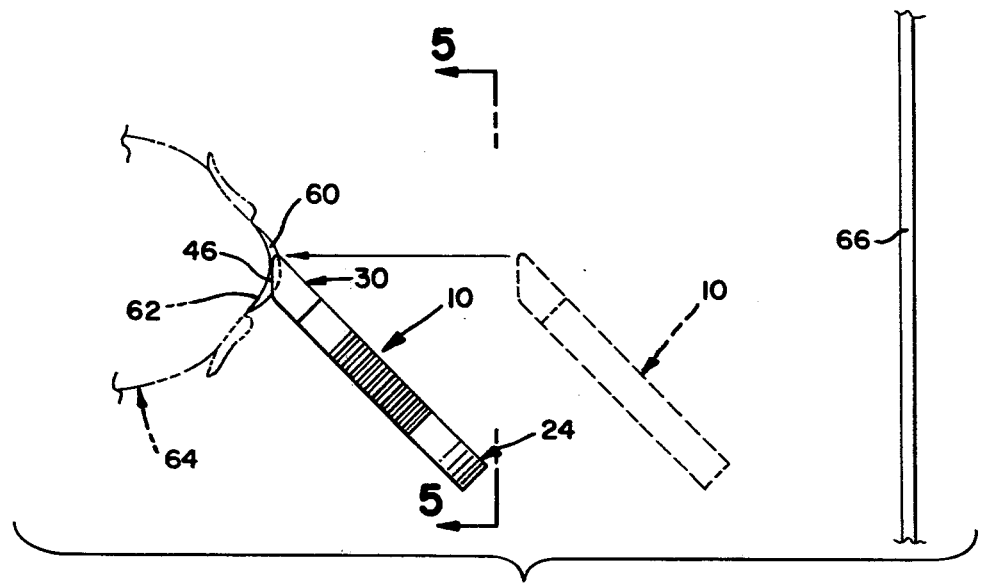
FIG. 4 is a side view of the device in operation.
Figure 5:
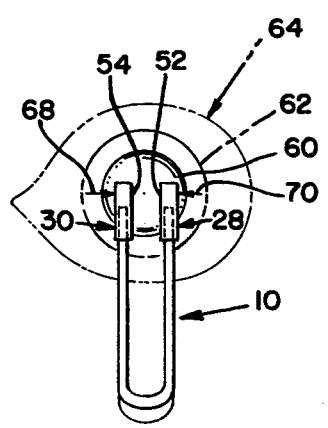
FIG. 5 is a view taken along line 5—5 of FIG. 4.

Turning to FIG. 4, it may be seen that tweezer device 10 may be used for the removal of soft contact lens 60 which lies on cornea 62 of human eye 64. Soft contact lens 60 is quite flexible and easily conforms to the outer surface of cornea 62. Although the characteristic of flexibility greatly aids in the fitting of soft contact lens 60 on eye 64, this characteristic also poses handling problems in that lens 60 is a gelatin-like object and may be punctured or torn if improperly handled. Soft contact lens 60 may be in the order of 8 to 16 millimeters in diameter. It has been found that legs 12 and 14 should be separated from one another by 7 to 8 millimeters and that caps 28 and 30 should be at least 4 millimeters long to sufficiently blunt end portions 16 and 18 of legs 12 and 14. Inner edges 52 and 54 of caps 28 and 30 bear on soft contact lens 60 during removal of soft contact lens 60 from eye 64. Device 10 is aligned with the center of eye 64 employing mirror 66. The fact that end surfaces 44 and 46 of caps 28 and 30 are slanted, rather than squared, permits the user to lower means 24 below the line of sight of eye 64 and the meeting place between device 10 and soft contact lens 60, namely edges 52 and 54 of caps 28 and 30. Device 10 exerts enough pressure on soft contact lens tending to fold the same together, FIG. 5, (squeezing force shown by arrows 68 and 70), and break the surface tension holding lens 60 to eye 64. Device 10 may also be employed to retrieve lens 60 from a holding case and to shake fluid from lens 60 for use.

In operation, the user sterilizes device 10 before touching the same to soft contact lens 60. Caps 28 and 30 are used to actually touch lens 60. Legs 12 and 14 are squeezed together to generally fold soft contact lens. Such squeezing action may be used to remove soft contact lens 60 from the cornea of an eye after alignment of caps 28 and 30 with soft contact lens 60 employing mirror 66. The rigidity obtained from legs 12 and 14 permit the easy manipulation of soft contact lens 60 while the softness and flexibility of caps 28 and 30 prevent any damage to lens 60 during manipulation.

While in the foregoing specification embodiments of the invention have been set forth in considerable detail for the purposes of making a complete disclosure of the invention, it will be apparent to those or ordinary skill in the art that numerous changes may be made in such details without departing from the spirit and principles of the invention.

What is claimed is:

1. A tweezer device for manipulation of soft contact lenses comprising:
    a. a pair of relatively rigid legs, each leg having a first end portion and a second end portion, said first end portion including an end surface;
    b. means for connecting said second end portion of each of said pair of legs;
    c. a cap covering said end surface of each of said pairs of relatively rigid legs, each cap including a first tip, a second tip, and an end surface, said first tip extending further from said first end portion of each of said legs than said second tip, said cap end surface spanning said first and second tips and obtaining support from said end surface of said first end portion of each leg, said cap being constructed of soft material having an elastic memory.

2. The tweezer device of claim 1 in which said end portion of each of said pair of legs includes a shoulder bearing on a portion of said cap.

3. The tweezer device of claim 2 in which each of said pair of legs includes a roughened portion spaced from said cap.

4. The tweezer device of claim 3 in which additionally comprises means for resisting force tending to bring said pair of legs together.

* * * * *